United States Patent [19]
Suenram et al.

[11] Patent Number: 5,831,439
[45] Date of Patent: Nov. 3, 1998

[54] PORTABLE FOURIER TRANSFORM MICROWAVE SPECTROMETER WITH CRYOGENIC RECEIVER FOR TRACE GAS ANALYSIS

[75] Inventors: Richard D. Suenram, Germantown; Francis J. Lovas, Bethesda, both of Md.; Jens U. Grabow, Kiel, Germany; Marlin D. Harmony, Lawrence, Kans.; Igor Leonov; Andre Zuban, both of Nizhny Novgorod, Russian Federation

[73] Assignee: The United States of America as respresented by the Secretary of Commerce, Washington, D.C.

[21] Appl. No.: 802,517

[22] Filed: Feb. 20, 1997

Related U.S. Application Data

[60] Provisional application No. 60/013,064 Mar. 8, 1996.

[51] Int. Cl.$^6$ .................................................... G01N 22/00
[52] U.S. Cl. .......................................... 324/636; 324/633
[58] Field of Search .................................... 324/629, 633, 324/636, 307, 318; 359/838, 843, 846, 868, 869; 356/346; 427/162, 163.4, 165

[56] References Cited

U.S. PATENT DOCUMENTS

| | | | |
|---|---|---|---|
| 4,369,404 | 1/1983 | Flygare et al. | 324/636 |
| 4,703,273 | 10/1987 | Kolbe et al. | 324/636 |
| 5,057,782 | 10/1991 | Brown et al. | 324/636 |
| 5,124,653 | 6/1992 | Andresen et al. | 324/636 |

OTHER PUBLICATIONS

M.D. Harmony, K.A. Beran, D.M. Angst, and K.L. Ratzlaff, "A Compact Hot–Nozzle Fourier Transform Microwave Spectrometer", Rev. Sci. Instru., Aug. 1995, pp. 5196–5202.

J. U–Grabow and W. Stahl, Z. Naturforsch, "A Pulsed Molecular Beam Fourier Transform Spectrometer with Parallel Molecular Beam and Resonator Axes",. 45a, 1043–1044, May 1990.

J. Z. Gillies et al., "Van der Waals Complexes in 1,3–Dipolar Cycloaddition Reactions: Ozone–Ethylene," American Chemical Society 1991, 113, pp. 2413–2421 (month unavailable).

J. Z. Gillies et al., "van der Waals Complexes of Chemically Reactive Gases: Ozone–Acetylene," American Chemical Society 1991, 113 pp. 6409–6415 (month unavailable).

R. D. Suenram et al., Fourier Transform Microwave Spectroscopy: A Potential New Analytifal Tool for Trace Gas Species, in Proceedings of the 1994 U.S. EPA/WMA International Symposium, "Measurement of Toxic and Related Air Pollutants" pp. 551–561 (month unavailable).

F. J. Lovas et al., "Using Fourier Transform Microwave Spectroscopy to Detect Hazardous Air Pollutants," in Proceedings of Optical Sensing for Environmental and Process Monitoring, Orman A. Simpson, Editor, A&WMA vol. VIP–37 (SPIE vol. 2365) pp. 58–69, Apr. 1995.

*Primary Examiner*—Diep N. Do
*Attorney, Agent, or Firm*—Larson & Taylor

[57] ABSTRACT

A highly compact, portable, pulsed-molecular-beam Fabry-Perot cavity Fourier transform microwave spectrometer which incorporates ultra-fine Fabry-Perot mirror surface finishes has been developed for trace gas analysis. The mirrors, having a surface finish of less than or equal to 0.25 microns rms, are coated with nickel and then with either gold or silver. In a further embodiment, one or more fixed-tuned Fabry-Perot cavities are incorporated within a single vacuum chamber to monitor one or more chemical species of interest.

10 Claims, 9 Drawing Sheets

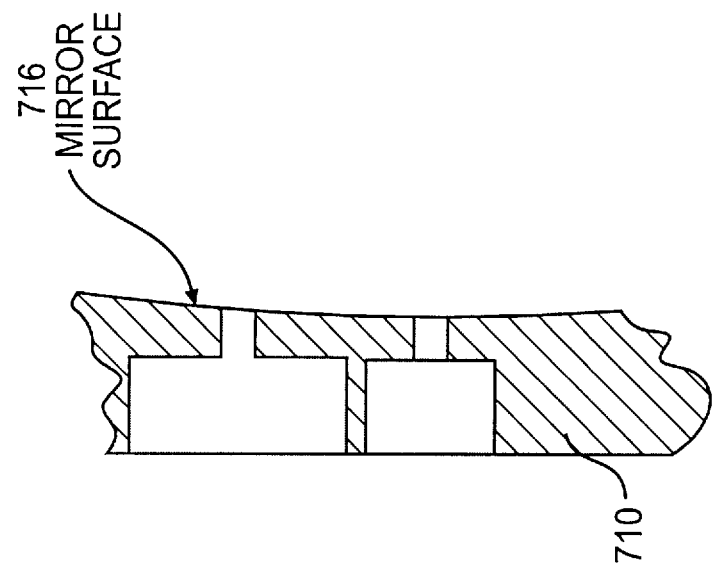
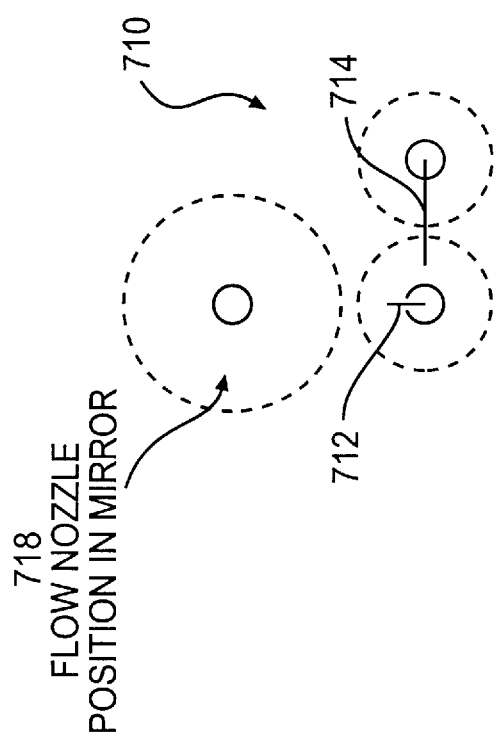
FIG. 7b
FIG. 7a

PORTABLE FOURIER TRANSFORM MICROWAVE SPECTROMETER WITH CRYOGENIC RECEIVER FOR TRACE GAS ANALYSIS

RELATED APPLICATION

This application claims benefit of priority of U.S. Provisional Application Ser. No. 60/013,064 filed Mar. 8, 1996.

FIELD OF THE INVENTION

This invention relates to a method and apparatus for identifying gaseous particles, compounds, molecules, transient molecules, atoms, or molecular complexes and determining their concentration in a gas mixture by analysis of an emission spectrum generated by rotational transitions of molecules in gaseous substances exposed to microwave radiation. The composition of gas mixtures as well as liquids and solids converted to gas mixtures can be quantitatively determined by microwave spectroscopy. Irradiation of gases by microwaves of a given frequency excite the molecules of one of said gases within the gas mixture. The excited gas undergoes rotational transitions which are typical for that specific molecule and because of these unique rotational transitions the excited gas can be detected and identified.

The instant invention comprises a highly compact, portable, pulsed molecular-beam Fabry-Perot cavity Fourier transform microwave spectrometer which incorporates a cryogenically-cooled, low-noise amplifier in the receiving system that has been developed for trace gas analysis. A number of new improvements in the overall instrument design have been incorporated to dramatically increase the sensitivity of the instrument and at the same time simplify the electronics associated with the instrument. With these new changes, real-time analysis of trace-gas species in the parts per billion (volume) range is possible. A user-friendly software package which employs a Graphical User Interface (GUI) has been written that allows complete mouse-driven instrument control with a standard 80486 processor based personal computer.

BACKGROUND OF THE INVENTION

The Fabry-Perot cavity is an interferometer composed of 2 semireflective mirrors. When the spacing between the mirrors is an integral number of wavelengths, light is transmitted. When it is half an integer number of wavelength, destructive interference makes the transmitted intensity very low. The contrast between the maximum and minimum transmitted intensity depends on the reflectivity of the mirrors. The resolution and free spectral range (distance in angstrom between two interference orders) depends on both the spacing between the mirrors and the finesse. The phase difference can be produced in three different ways: changing the physical spacing between the mirrors, the refraction index or the incidence angle. This path difference is expressed mathematically by the basic Fabry-Perot equation:

$$\lambda p = 2\, nt \cos \theta$$

where theta is the incidence angle of the light, lambda the wavelength, n the refraction index, and t the distance between the mirrors. It is easy to understand that given the symmetry of revolution of the Fabry-Perot etalon, a constructive interference for a given angle theta, results in a ring of light (assuming the Fabry-Perot is illuminated by an extended monochromatic source). Therefore, the multiple ring pattern typical of Fabry-Perot interferometers is present. Here the phase change is produced by the various incidence angles. A phase difference will also be produced by a change in spacing. For a given interference order (given ring) a change in spacing produces a change in angle of the ring since the product interference order by wavelength is constant. Therefore an increase in ring diameter occurs as the spacing is increased.

It is further noted that the surface finish of the mirrors and the sphericity play an important role in the overall sensitivity of the instrument.

The following articles are hereby incorporated by reference into the instant invention. Any references within these articles are also incorporated by reference into the instant application.

"A Compact Hot-Nozzle Fourier Transform Microwave Spectrometer", M. D. Harmony, K. A. Beran, D. M. Angst, and K. L. Ratzlaff, Rev. Sci. Instru., 66, 5196–5202 (1995).

"A Pulsed Molecular Beam Fourier Transform Spectrometer with Parallel Molecular Beam and Resonator Axes", J. U-Grabow and W. Stahl, Z. Naturforsch. 45a, 1043–1044 (1990).

"The Microwave Spectrum and Molecular Structure of the Ethylene-Ozone van der Waals Complex," J. Z Gillies. C. W. Gillies, R. D. Suenram, and F. J. Lovas, J. Am. Chem. Soc. 111, 3073–3074 (1989).

Two previous patents exist which concern the technique of Fourier Transform microwave spectroscopy. Both of these patents and any references within these patents are incorporated by reference into the instant application. U.S. Pat. No. 4,369,404 to Flygare et al. teaches a conventional method and apparatus for the spectroscopic observation and detection of particles. A second patent, U.S. Pat. No. 5,124,653 to Andresen et al. teaches a method and apparatus for determining the concentration of compounds in a gas mixture by microwave gas analysis. Neither of these patents contemplates or addresses the advantages of the various embodiments of the instant invention. Namely, having mirrors and vacuum chamber sufficiently small to allow the instrument to be portable, providing a vacuum chamber which incorporates several sets of fixed-tuned Fabry-Perot cavities for detecting specific chemical species of interest, providing a fixed mirror and simultaneously forming an end of the vacuum chamber, reducing the electronic components by incorporating broad-banded single-pole double-throw microwave switches, eliminating one stage of heterodyne mixing in the receiving system, fitting the microwave mirrors with at least two microwave antennas in a preferred orientation, mounting a cryogenically cooled low noise amplifier directly to the mirror, utilizing commercially available pulsed molecular beam flow valves, utilizing mirrors with ultra-fine surface finishes, and a user friendly point-and-click software system to control the overall system, are not addressed in either U.S. Pat. No. 4,369,404 or U.S. Pat. No. 5,124,653.

Certain aspects of this invention have been disclosed in the following two scientific articles, each of which was published by a respective group of authors involving some of the inventors of the present invention.

"Fourier Transform Microwave Spectroscopy: A Potential New Analytical Tool For Trace Gas Species," R. D. Suenram, F. J. Lovas, and R. L. Sams, Measurement of Toxic and Related Air Pollutants, Proceedings of the 1994 U.S. EPA/A&WMA International Symposium, 551–561 (1994).

"Fourier Transform Microwave Spectroscopy to Detect Hazardous Air Pollutants," F. J. Lovas, W. Pereyra, R. D. Suenram, G. T. Fraser, J. U-Grabow, and A. R. Hight Walker, Proceedings of Optical Sensing for Environmental and Process Monitoring, Air & Waste Management Assoc. and The Int'l. Soc. for Optical Engineering, 58–69 (1994).

While these articles disclose several aspects of the instant invention, other aspects and combinations of elements claimed herein are not disclosed or suggested in these articles.

SUMMARY OF THE INVENTION

The technique of Fourier transform microwave spectroscopy is used to observe and analyze the rotational spectra of molecules in the gas phase. By monitoring the intensity of a given rotational transition, the concentration of the molecular species in the gas mixture can be determined. Sufficient sensitivity is obtained with the instrument of the instant invention to allow concentration determination of chemicals in a gas mixture that are present in concentrations down to the parts-per-billion by volume (ppbv) level.

The instant invention utilizes a pulsed molecular beam Fabry-Perot cavity microwave spectrometer having sufficiently small size mirrors and vacuum chamber to allow the instrument to be portable. The instrument is housed in a standard laboratory instrumentation rack of the type that is on wheels so the entire instrument is portable.

A number of features and combinations of elements are employed in the present invention to improve the overall sensitivity of the Fabry-Perot cavity Fourier Transform spectrometer. A key feature of the instant invention is the ultra-fine surface finish on the Fabry-Perot cavity mirrors. These mirrors are diamond-turned, polished and then coated with two different metals.

The microwave molecular beam is pulsed coaxially into the Fabry-Perot cavity axis through a pin hole in one of the mirrors which form the cavity. This feature is employed in the current instrument in order to improve the signal-to-noise ratio by a factor of 20 to 50. In one embodiment, the instant invention utilizes an arrangement having the vacuum chamber with one mirror of the Fabry-Perot cavity fixed and forming the end of the vacuum chamber. This allows the attachment of a low-noise, cryogenically-cooled microwave amplifier directly to the receiving antenna located in the mirror, thus eliminating all insertion losses normally associated with the microwave cables which are used to carry the extremely weak molecular emission signals (microwave signals) from the mirror antenna to a region outside the vacuum chamber. This improves the overall sensitivity of the instrument by a factor of 2–5. In addition, this arrangement allows easy access to the pulsed molecular beam valve for optimizing of molecular signal strength (tuning) or servicing and repair of the beam valve without cooling down or venting of the vacuum chamber.

The electronic circuitry in accordance with the present invention has been simplified by incorporating broad-banded single-pole double-throw microwave switches. These components eliminate the requirement of having microwave isolators and circulators in the system and they further permit the instrument to operate in four distinct microwave bands without switching microwave hardware components.

A broad-banded, image-rejection, single-sideband microwave mixer is employed to heterodyne the two microwave signals. This type of mixer eliminates the noise which is normally present in a double sideband mixer by rejecting the noise from the unused sideband and thus, effectively increasing the instrument sensitivity by a factor of two.

In an effort to minimize the number of electronic components and simplify hardware and spectral analysis, the instant invention eliminates one stage of heterodyne mixing in the receiving system. This is possible because the spectra of the sampled signal can be represented by the infinite sequence of shifted spectra of the analog signal. This shift is known as the Nyquist interval. In practice it is not important which interval is used. In order to avoid aliases in the spectrum, it is required that the original spectrum be narrower than the Nyquist interval. It is also necessary that the digitizer being used be able to digitize various signals.

The orientation of the microwave antennas and the mirrors is an important factor in the present invention. Both Fabry-Perot cavity microwave mirrors are fitted with two microwave antennas. The use of at least two antennas eliminates a difficulty which occurs with only one set of antennas, namely the propagation of higher order microwave modes can overlap into the transmission mode of interest. The second (or further) set of antennas effectively acts as a mode filter and eliminates unwanted modes and increases the signal to noise ratio. This permits digitization of the molecular signal to begin following a shorter time delay. With only one set of antennas, a longer time delay is necessary in order to first allow the cavity ringing to dissipate which is caused by microwave propagation in these unwanted modes. An additional advantage is gained by using antennas of different lengths which are tuned for low and high frequency microwave propagation. Through computer switching, the antennas used to irradiate the microwaves into the cavity can be changed between low and high frequency. The actual number of antennas used is limitless. With uniquely designed antennas, various frequencies can be directed into the cavity.

The present invention employs commercially available pulsed molecular beam valves patterned after those described by "The Microwave Spectrum and Molecular Structure of the Ethylene-Ozone van der Waals Complex," J. Z. Gillies, C. W. Gillies, R. D. Suenram, and F. J. Lovas, J. Am. Chem. Soc. 111, 3073–3074 (1989), which incorporate flow lines so that process gas streams can be sampled in real-time using commercially available mass flow controllers. Any valve resulting in real-time sampling of the gas stream can be used.

In many industrial applications, i.e., process control environments, only one or two chemical species need to be monitored. For these applications, the Fabry-Perot cavity is advantageously pre-set to propagate a fixed microwave frequency which in resonant with a rotational transition of the chemical species of interest. Thus, there is no need to "tune the cavity." If several specific chemical species are to be monitored, the present invention provides that several sets of fixed-tuned Fabry-Perot cavities are incorporated into the vacuum chamber. This configuration eliminates the high cost of the microwave synthesizer and, instead, uses inexpensive, relatively fixed-tuned microwave sources.

Finally, the overall control of the system is accomplished using a software package run on a standard computer. A software system has been developed for a 486 personal computer which allows instrument control via a standard mouse using point-and-click techniques. The software employs a Graphical User Interface and is very user-friendly.

An object of the present invention is to use ultra-fine surface finish Fabry Perot cavity mirrors. This ultra-fine surface finish greatly increases the sensitivity and efficiency of the instrument and greatly increases the signal-to-noise ratio.

A further object of the present invention is to improve the real-time analytical capabilities of the instrument by using multiple sets of mirrors so that several components of an unknown gas mixture can be analyzed simultaneously.

A further object of the invention is to pre-set the Fabry-Perot cavity to propagate a fixed microwave frequency which is resonant with a rotational transition of a chemical species of interest.

A still further object of the invention is to incorporate several sets of fixed-tuned Fabry-Perot cavities into a single vacuum chamber so that several components of an unknown gas mixture can be simultaneously monitored without relying on a microwave synthesizer.

The new instrument has tremendous potential in chemical industry applications for trace-gas analysis. Instantaneous (100 ms) detection limits for most chemical species generally ranges from 10–500 ppbv using an inert carrier gas such as Ar or a commercially available 80/20 Ne/He mixture. Lower detection limits can be reached by averaging the data from a larger number of gas pulses. The instrument is also 100% species specific since the detection technique relies on the observation of an individual rotational transition of the species being investigated. The user-friendly software package permits industrial technicians to master instrument control with only a few hours of tutorial.

BRIEF DESCRIPTION OF THE DRAWINGS

FIG. 4b shows the Fourier-Transform time domain signal as applied to FIG. 4a.

FIGS. 7a and 7b show front and side views of details of the location and orientation of two antennas and the pulsed flow nozzle in a cavity mirror.

DETAILED DESCRIPTION OF THE INVENTION

The present invention comprises a portable Fourier transform microwave spectrometer which incorporates a number of new enhancements which improve the sensitivity, decrease the size, and eliminate a number of electronic components, all of which make the instrument less expensive and more robust.

Figure 1:
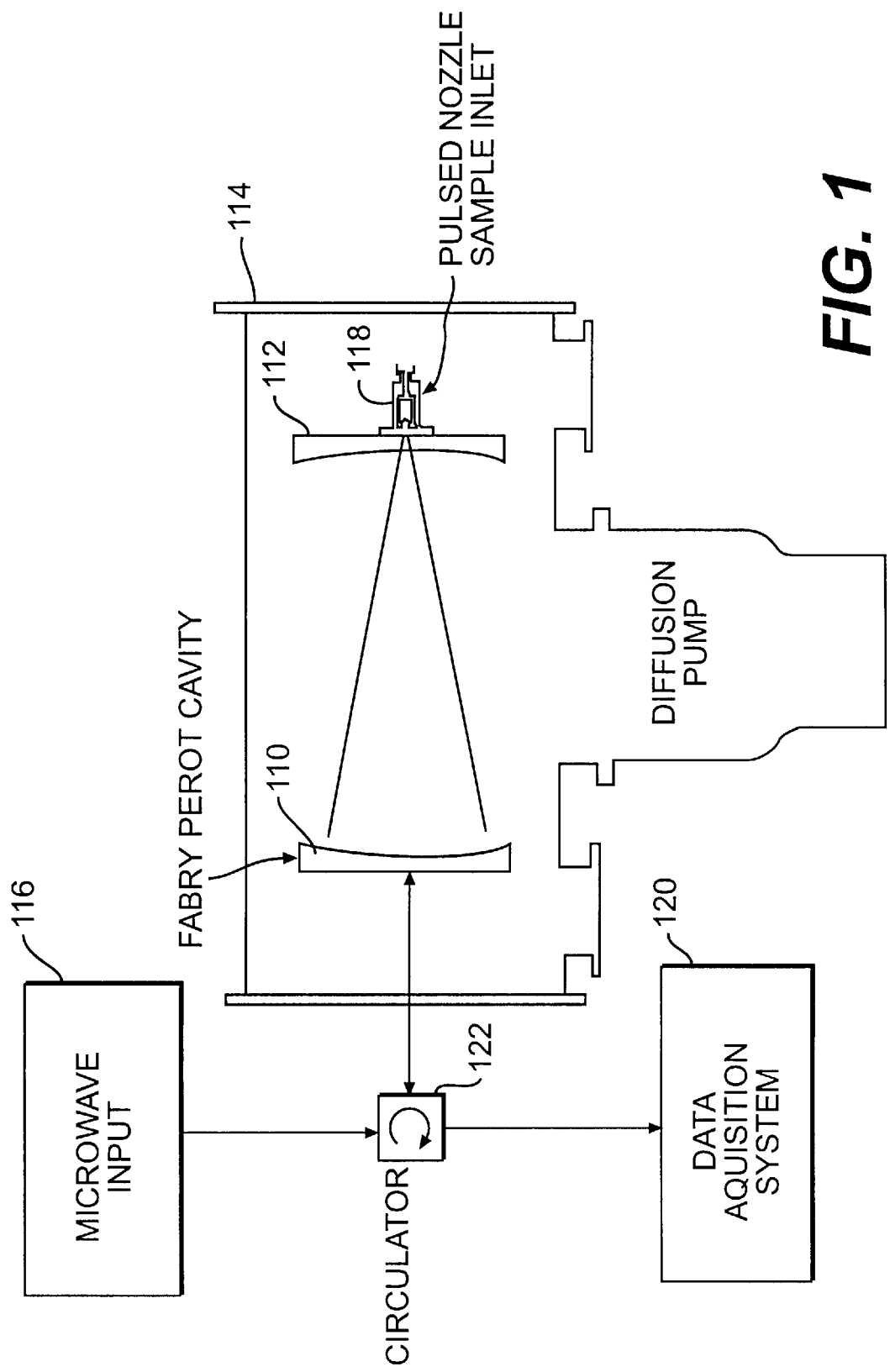
FIG. 1 shows a schematic of the Fourier-Transform Microwave Spectrometer.

The following is a description of the present invention. FIG. 1 shows one configuration of a pulsed molecular beam Fabry-Perot cavity microwave spectrometer constructed using mirrors 110 and 112 and vacuum chamber 114 of sufficiently small size to allow the instrument to be portable according to one embodiment of the present invention. The irradiating microwaves from the microwave input 116 are directed into the chamber at mirror 110 while the gas input nozzle 118 is located at mirror 112. The data acquisition system 120 is attached to a circulator 122 to monitor and detect the chambered gases and microwaves.

A key feature in this and other embodiments of the present invention is the ultra-fine surface finish of the Fabry-Perot cavity mirrors 110 and 112. The instant invention employs diamond-turned mirrors with a surface finish $\leq 1$ micron rms. This surface is further polished to a finish of $\leq 0.25$ microns rms and the overall sphericity across the surface is $\leq 4$ microns rms. After polishing, the surface of each mirror is coated with nickel and then with either gold or silver. By ultra-finely polishing and coating the mirrors, the signal-to-noise ratio of the instrument is greatly increased.

Figure 2:
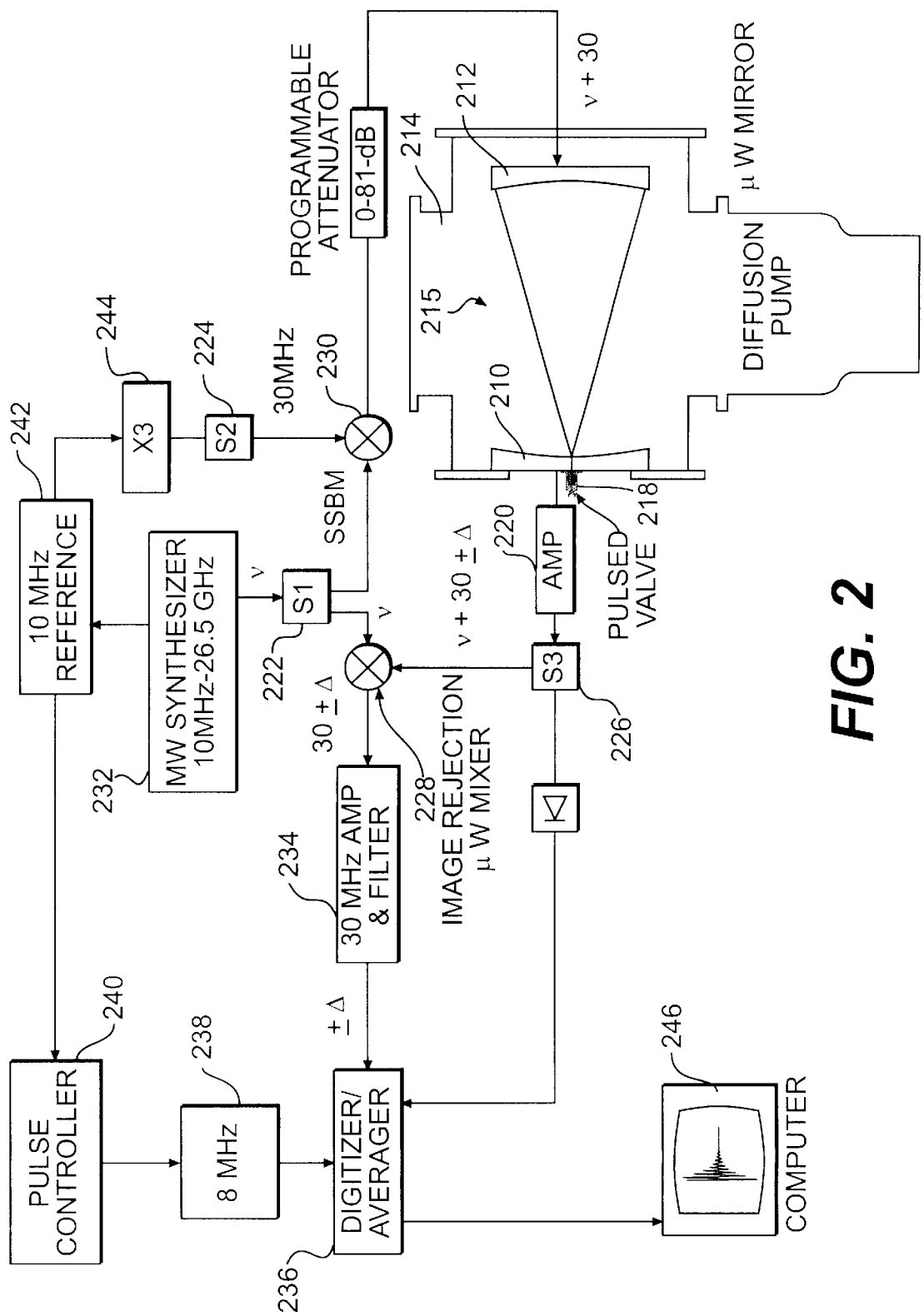
FIG. 2 shows a detailed electronic schematic of the circuitry associated with the Fourier-Transform Microwave Spectrometer.

A more advantageous design of the present invention is shown in FIG. 2. This embodiment uses an improved nozzle arrangement which is formed by designing the vacuum chamber 214 with mirror 210 of the Fabry-Perot cavity fixed and forming an end of the vacuum chamber 214. This allows the attachment of a low-noise, cryogenically-cooled microwave amplifier 220 directly to the receiving antenna located in mirror 210. This eliminates all insertion losses normally associated with the microwave cables which are used to carry the extremely weak molecular emission signals (microwave signals) from the mirror antenna to a region outside the vacuum chamber 214, thus improving the overall sensitivity of the instrument by a factor of 2–5. In addition, this arrangement allows easy access to the pulsed molecular beam valve 218 for optimizing of molecular signal strength (tuning) or servicing and repair of beam valve 218 without cooling down or venting of vacuum chamber 214. As a working model, the instrument is housed in a standard laboratory instrumentation rack that is two panels wide (38") and half the height of a normal instrument rack (36"). The instrument rack is on wheels so the entire instrument is portable.

Figure 3:
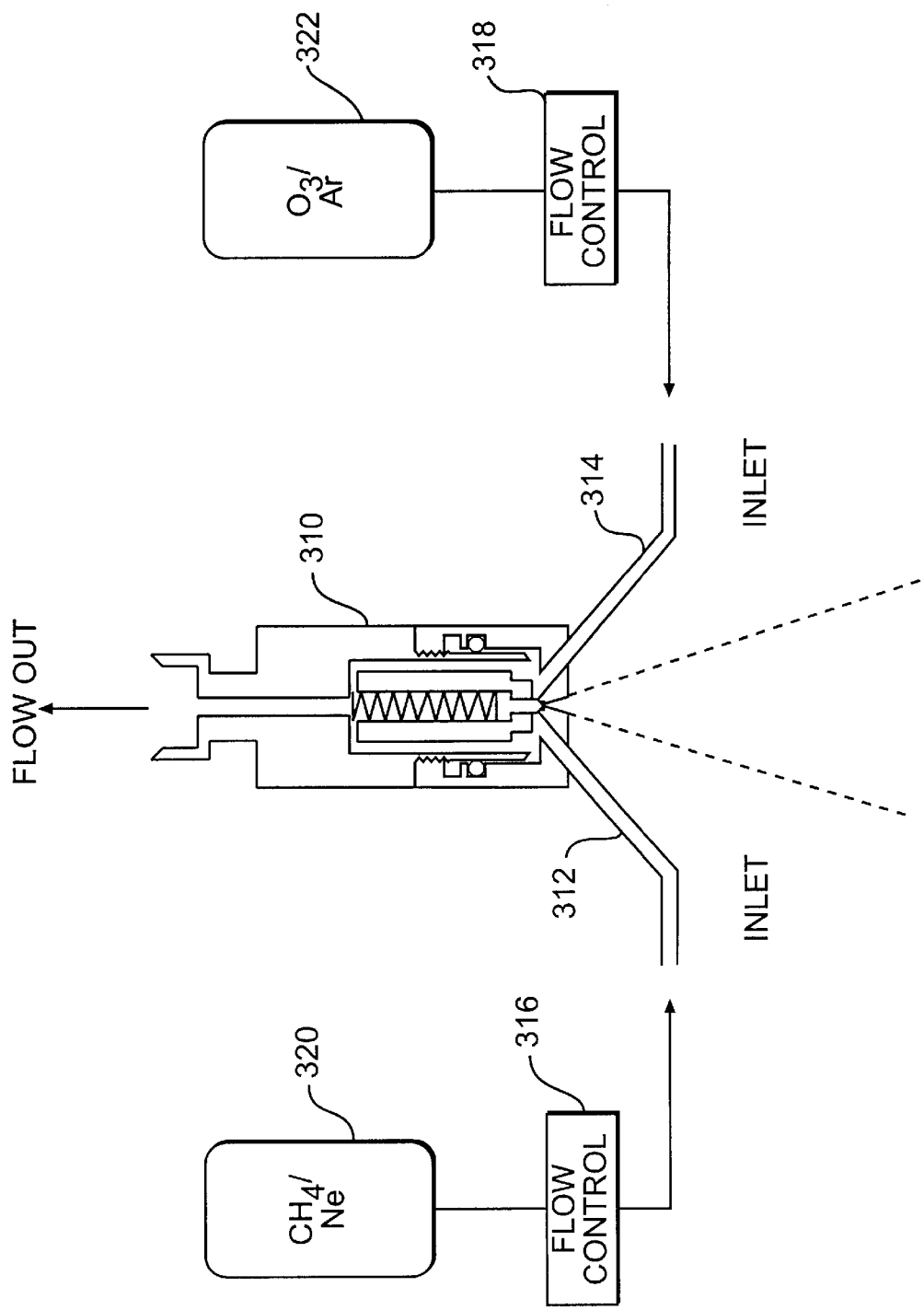
FIG. 3 shows a blow-up of a multiple gas inlet nozzle.

A further nozzle design is shown in FIG. 3 which allows the mixture of reactive gases to be premixed just prior to injection into the chamber. The advantages of this embodiment is that gases that react violently when mixed can now be analyzed in a controlled manner. Nozzle 310 incorporates flow lines 312 and 314 so that the process gas streams can be sampled in real-time using commercially available mass flow controllers 316 and 318. Gas supply 320 supplies gas to flow controller 316 and gas supply 322 supplies gas to flow controller 314.

The present invention pulses the molecular beam coaxially into the Fabry-Perot cavity axis via a pulsed valve 218 through a pin hole in mirror 210 which, along with mirror 212, forms the cavity. This feature is employed in the current instrument in order to improve the signal-to-noise ratio by a factor of 20 to 50.

The electronic circuitry design shown in FIG. 2 has been simplified by the incorporation of broad-banded (2–26.5 GHz) single-pole double-throw microwave switches 222, and 226. These components eliminate the necessity of having microwave isolators and circulators in the system and they permit the instrument to operate in four microwave bands (4–8 GHz, 8–12.4 GHz, 12.4–18.6 GHz, and 18.6–26.5 GHz) without switching microwave hardware components. Further a broad-banded, image-rejection, single-sideband microwave mixer 228 is employed to heterodyne the two microwave signals down to a 30 MHz IF frequency. This type of mixer eliminates the noise which is normally present in a double sideband mixer by rejecting the noise from the unused sideband and effectively increases the instrument sensitivity by a factor of 2. The present invention eliminates one stage of heterodyne mixing in the receiving system thus, the 30 MHz IF signal is digitized directly at 8 MHz provided by generator 238. This is possible because the spectra of the sampled signal can be represented by the infinite sequence of shifted spectra of the analog signal. This shift is known as the Nyquist interval. In our application, the Nyquist interval is 8 MHz. Thus we have 30, 22, 14, 6, −2, −10, −18, −24 MHz intervals of the sequence available to use. In practice it is not important which interval is used. In order to avoid aliases in the spectrum, it is required that the original spectrum be narrower than the Nyquist interval. In the present invention, a bandpass filter with a 1.8 MHz bandwidth is employed which ensures that the necessary conditions are met. It is also necessary that the digitizer being used be able to digitize signals that are (30 MHz+the bandwidth)/2=15.9 MHz. Since we use a 20 MHz digitizer we choose the −2 MHz interval as the interval of choice.

FIGS. 7a and 7b show front and side views respectively of certain details of one of the Fabry-Perot cavity microwave mirrors. Mirror 710 is shown with two microwave antennas 712 and 714 oriented perpendicular to one another. This feature eliminates a long-standing difficulty which occurs with only one set of antennas, namely the propagation of higher order microwave modes which overlap the transmission mode of interest. The second set of antennas effectively acts as a mode filter and eliminates these unwanted modes. This permits digitization of the molecular signal to begin following a shorter time delay. With only one set of antennas, a longer time delay is necessary in order to first allow the cavity ringing to dissipate which was caused by microwave propagation in these unwanted modes. The specific design of multiple antennas is virtually limitless. The flow nozzle position in mirror 710 is shown at 718.

To obtain an ultra-fine surface finish on surface 716, mirror 710 is diamond turned to a surface finish of $\leq 1$ micron rms and subsequently polished to $\leq 0.25$ microns rms surface finish. Surface 716 is then coated first with nickel and then with either gold or silver. This surface quality improves the overall sensitivity of the instrument. While this technique has proven extremely effective, the surface finish of the mirrors is not limited to this specific technique. Other machining, polishing, etching, etc. techniques that produces an extremely fine surface finish can be used.

Figure 4A:
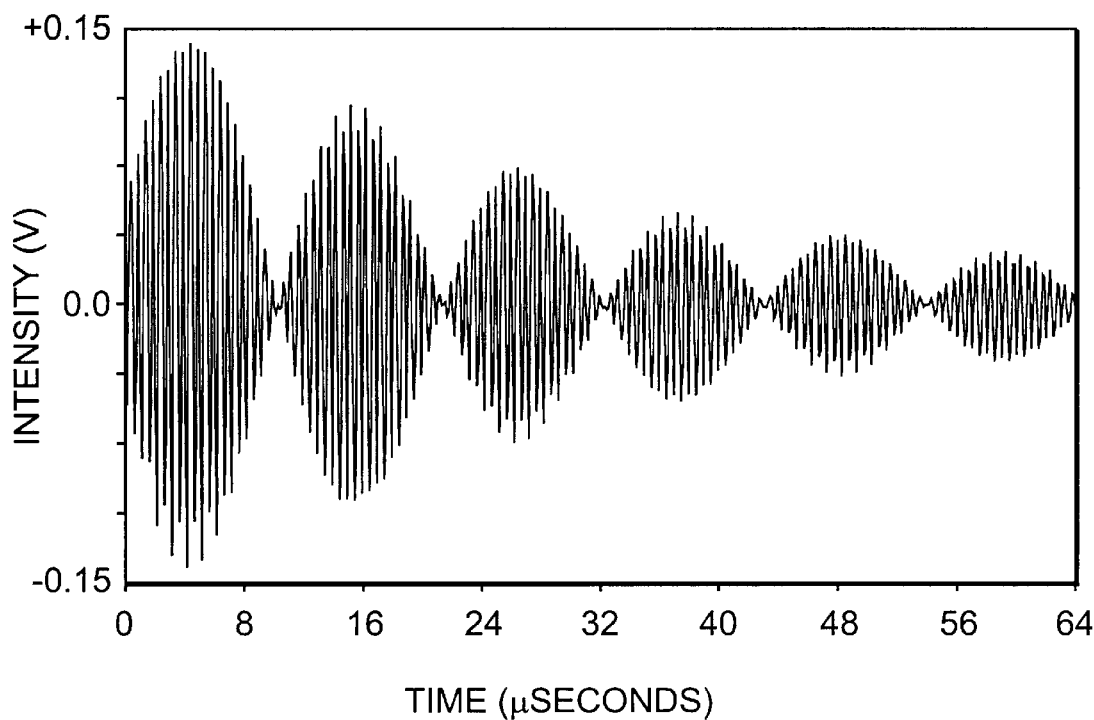
FIG. 4a shows the Free-induction Decay (FID) of microwaves and input gas within the Fabry-Perot cavity.
Figure 4B:
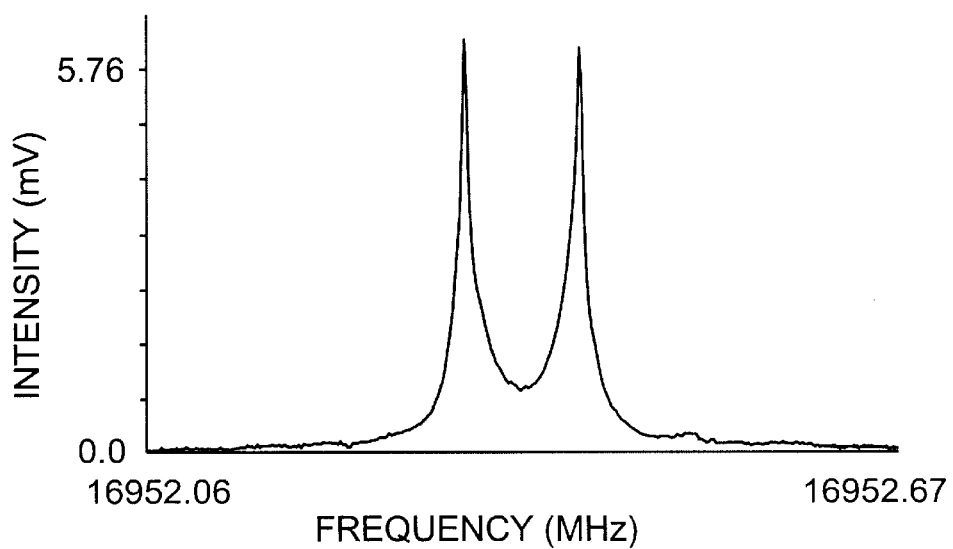

FIG. 4a shows the free-induction decay (FID) of a molecular emission signal from an input gas within the Fabry-Perot cavity using acrolein. FIG. 4b shows the Fourier-transformed time domain signal as shown in FIG. 4a. This transformation can be performed in real-time at an 8 Hz repetition rate.

Figure 5A:
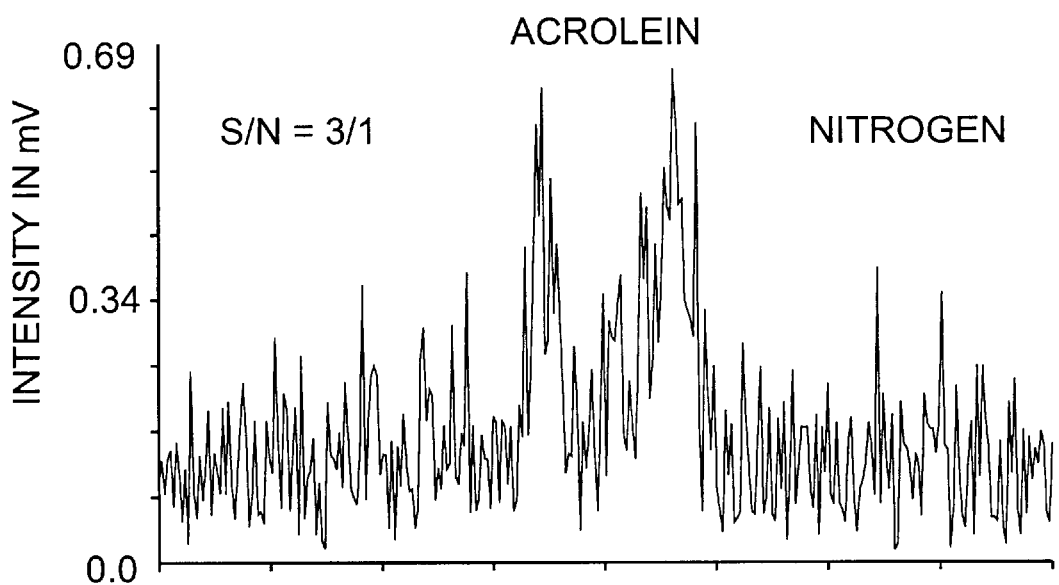
FIG. 5a shows the Fourier Transform output using Nitrogen as the carrier gas.
Figure 5B:
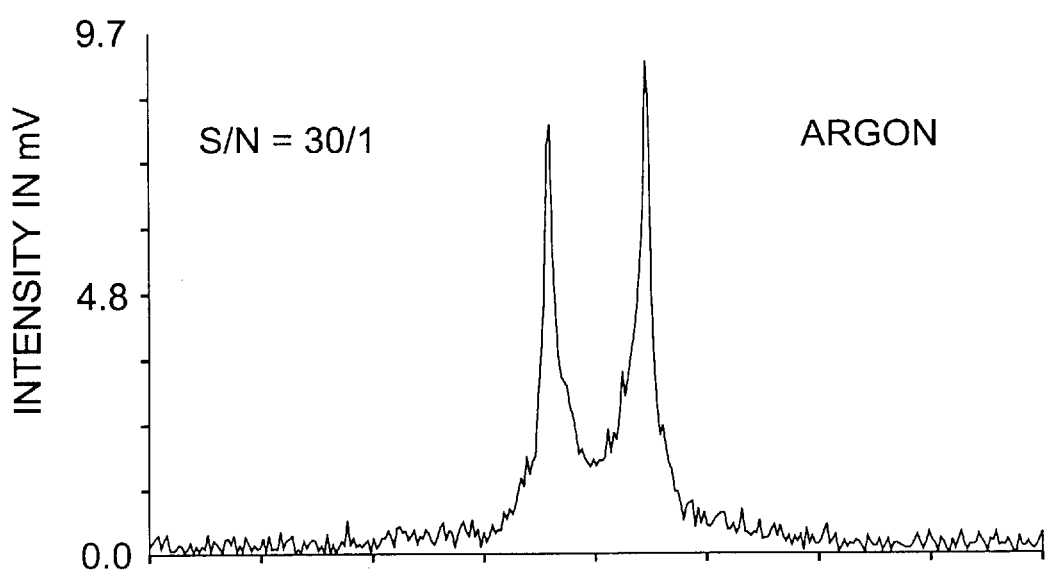
FIG. 5b shows the Fourier Transform output using Argon as the carrier gas.
Figure 5C:
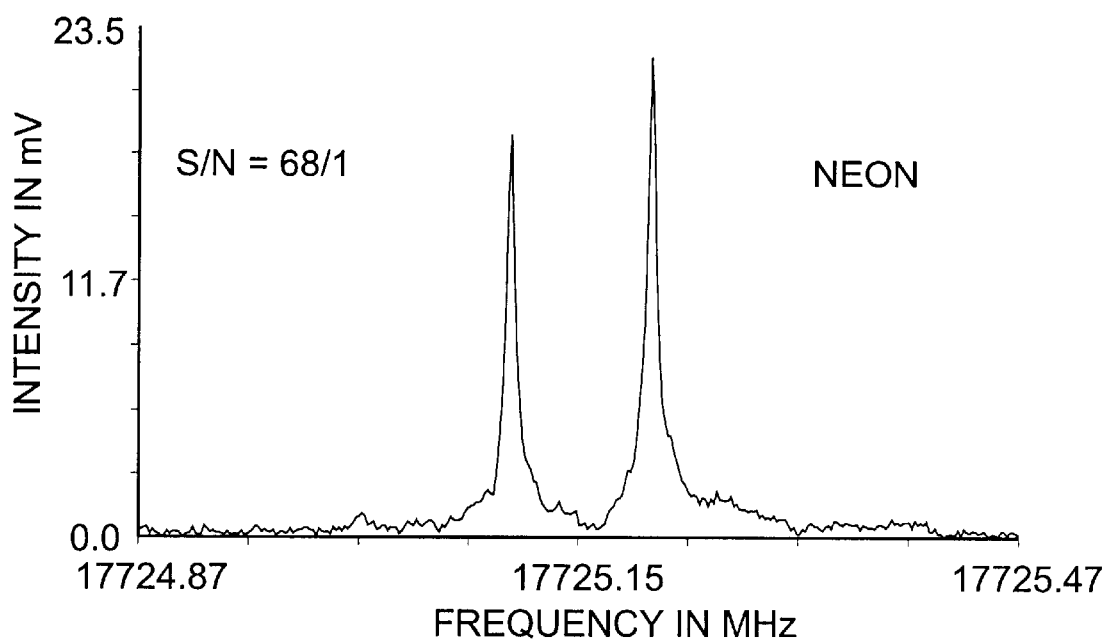
FIG. 5c shows the Fourier Transform output using Neon/He (80/20) as the carrier gas.

FIGS. 5a through 5c show the intensity levels as measured by the present invention for three specific carrier gases. FIG. 5a shows nitrogen, FIG. 5b shows argon, and FIG. 5c shows a 80/20 neon/He mixture. As shown from these three figures the neon/He gas mixture clearly yields the best signal-to-noise ratio.

Figure 6:
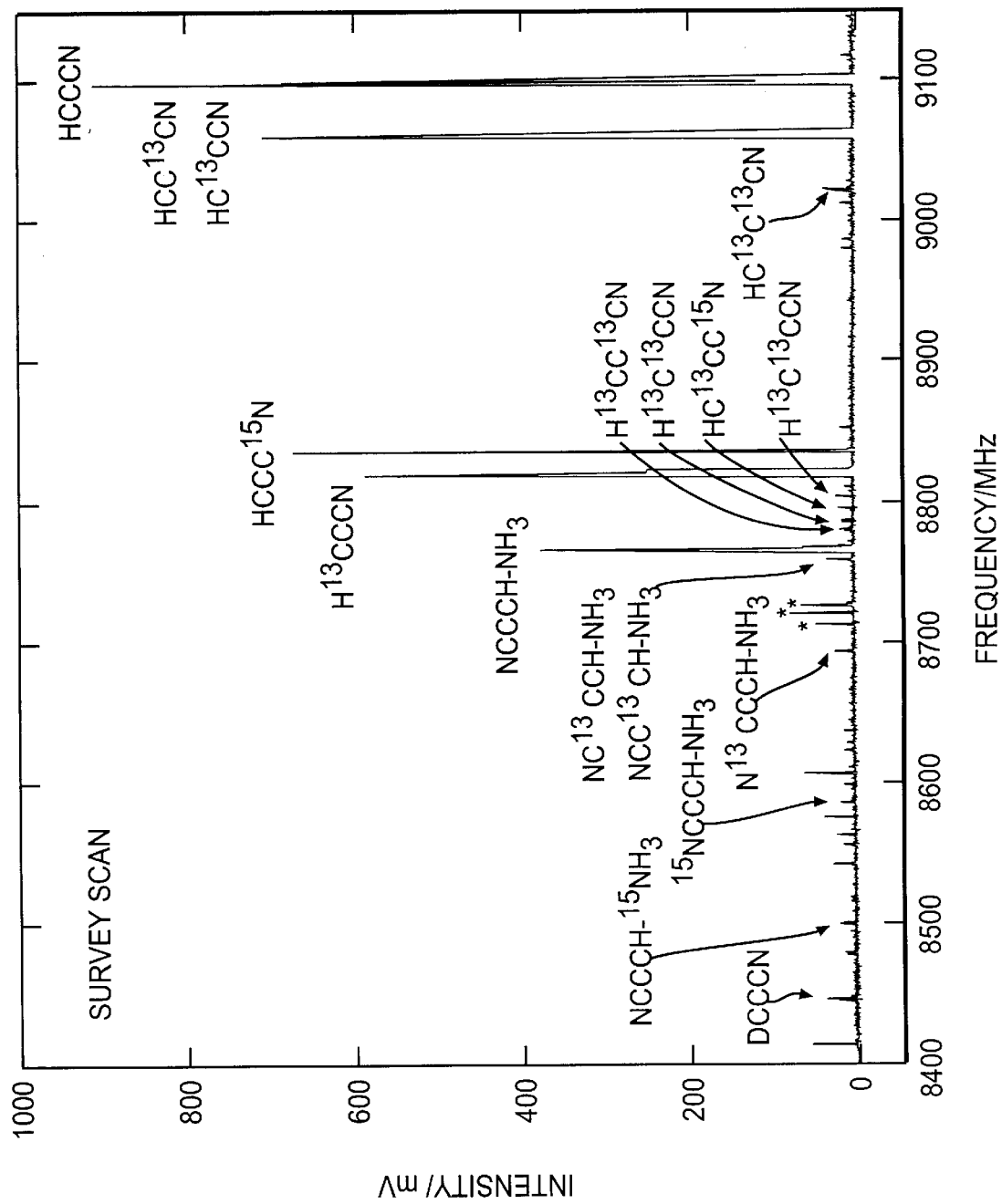
FIG. 6 shows the results of an automated 1 Gigahertz scan analyzing various compounds.

FIG. 6 shows a survey scan analyzing several compounds at once. Because of the unique automated scanning design of the present invention, various compounds can be analyzed from a single sample. If only a single pair of Fabry-Perot mirrors are being used, the mirrors within the chamber can be adjusted along with the associated microwave frequency to analyze different compounds within the chamber.

Table 1, below, details in tabular form the sensitivities to several OCS Isotopomers as analyzed using the present invention. Table 2, below, shows in tabular form the detection ability of several oxygenated species as analyzed using the present invention. Table 3, below, shows in tabular form the detection ability and correspondent formulas using several commercially available compounds.

TABLE 1

Natural Abundances of OCS Isotopomers and Frequencies of the J = 1 ← 0 Transitions

| Isotopomer | Obs Freq (MHz) | % Nat Abun | |
|---|---|---|---|
| OCS | 12162.979(2) | 93.74 | |
| $OC^{34}S$ | 11865.6628(20) | 4.158 | |
| $O^{13}CS$ | 12123.842(2) | 1.053 | |
| $OC^{33}S$ | 12009.824(5) | 0.7399 | |
| $^{18}OCS$ | 11409.7097(20) | 0.1880 | |
| $O^{13}C^{34}S$ | 11823.4625(20) | 0.04672 | |
| $^{17}OCS$ | 11767.3346(20) | 0.03495 | |
| $OC^{36}S$ | 11599.3816(20) | 0.01677 | |
| $^{18}OC^{34}S$ | 11119.9346(20) | 0.008338 | |
| $O^{13}C^{33}S$ | 11969.1284(20) | 0.008313 | |
| $^{18}O^{13}CS$ | 11382.1280(20) | 0.002112 | 50/1 in 100 pulses[1] |
| $^{17}OC^{34}S$ | 11473.9913 | 0.001551 | |
| $^{18}OC^{33}S$ | 11259.4485(20) | 0.001484 | |
| $^{17}O^{13}CS$ | 11734.5114(20) | 0.0003927 | |
| $^{17}OC^{33}S$ | 11617.(20) | 0.0003927 | |
| $O^{13}C^{36}S$ | 11554.3379(20) | 0.0001884 | |
| $^{18}O^{13}C^{34}S$ | 11089.7400(20) | 0.00009368 | 3/1 1000 pulses[1] |

[1]Sample mixture consisted of 1% OCS in 80/20 Ne/He carrier gas.

TABLE 2

Oxygenated Species Detection Limits

| Compound Type | Previous MW Work | Estimated MDS (ppb) | Suggested Transition | Transition frequency |
|---|---|---|---|---|
| Aldehydes | | | | |
| Formaldehyde | yes | 250 | $2_{1,1}-2_{12}$ | 14488.479 |
| Acetaldehyde | yes | 1 | $1_{01}-0_{00}$ | 19265.1327 |
| Acrolein | yes | 1 | $2_{02}-1_{01}$ | 17801.3081 |
| Propionaldehyde | yes | 5 | $1_{01}-0_{00}$ | 10492.466 |
| Crotonaldehyde | yes | 10 | $3_{03}-2_{02}$ A,E | 12768.7671 |
| | | | | 12768.7466 |
| Methacrolein | yes | 10 | $2_{02}-1_{01}$ | 14427.2749 |
| n-Butyraldehyde | yes, NIST | 15 | $2_{02}-1_{01}$ | 9664.6201 |
| Benzaldehyde | yes | 30 | $4_{04}-3_{03}$ | 10831.4023 |
| p-Tolualdehyde | yes, NIST | 150 | $6_{06}-5_{05}$ | 10723.7085 |
| Valeraldehyde | yes, NIST | | $4_{04}-3_{03}$ | 11160.9394 |
| Hexanal | no | | | |
| Ketones | | | | |
| Acetone | yes | 10 | $1_{11}-0_{00}$ EE | 15074.075 |
| Methyl Ethyl Ketone | yes | 80 | $1_{11}-0_{00}$ E | 12022.6182 |
| Alcohols | | | | |
| Methanol | yes | 1000 | $2_0-3_{-1}$ E | 12178.593 |
| Ethanol | yes | 300 | $1_{01}-0_{00}$ | 17485.875 |
| Ethers | | | | |
| MTBE | yes, NIST | 50 | $2_{12}-1_{01}$ | 12575.1662 |
| ETBE | yes, NIST | 120 | $4_{04}-3_{03}$ | 12399.0898 |
| TAME | yes, NIST | 700 | $3_{13}-2_{12}$ | 10966.4575 |

TABLE 3

FT MICROWAVE SPECTROMETER SENSITIVITY TESTS

| Compound | Formula | mds[1] (ppb) |
|---|---|---|
| Acrolein | $H_2C=CHCHO$ | 0.88 |
| Carbonyl Sulfide | OCS | 1 |
| Sulfur Dioxide | $SO_2$ | 4 |
| Propionaldehyde | $CH_3CH_2CHO$ | 100 |
| Methyl t-Butyl ether | $CH_3OC(CH_3)_3$ | 65 |
| Ethyl t-Butyl ether | $CH_3CH_2OC(CH_3)_3$ | 120 |
| Vinyl Chloride | $CH_2=CHCl$ | 0.45 |
| Ethyl Chloride | $CH_3CH_2Cl$ | 2 |
| Vinyl Bromide | $CH_2=CHBr$ | 1 |
| Ethylene Oxide | $CH_2CH_2\backslash\ /\ O$ | 11 |
| Toluene | $CH_3-C_6H_6$ | 130 |
| Vinyl cyanide | $CH_2=CH_2CN$ | 0.28 |
| Acetaldehyde | $CH_3CHO$ | 1 |
| Propylene Oxide | $CH_3CH_2CH_2\backslash\ /\ O$ | 11 |
| para-Tolualdehyde | $CH_3C_6H_6CHO$ | 150 |
| Methanol | $CH_3OH$ | 1000 |
| Benzaldehyde | $C_6H_6CHO$ | 26 |
| Propene | $CH_3CH=CH_2$ | 250 |

[1]Minimum detectable signal for the following set of parameters: Neon carrier gas; average of 100 gas pulses taken at a 2 Hz repetition rate (50 sec total integration time).

Figure 8:
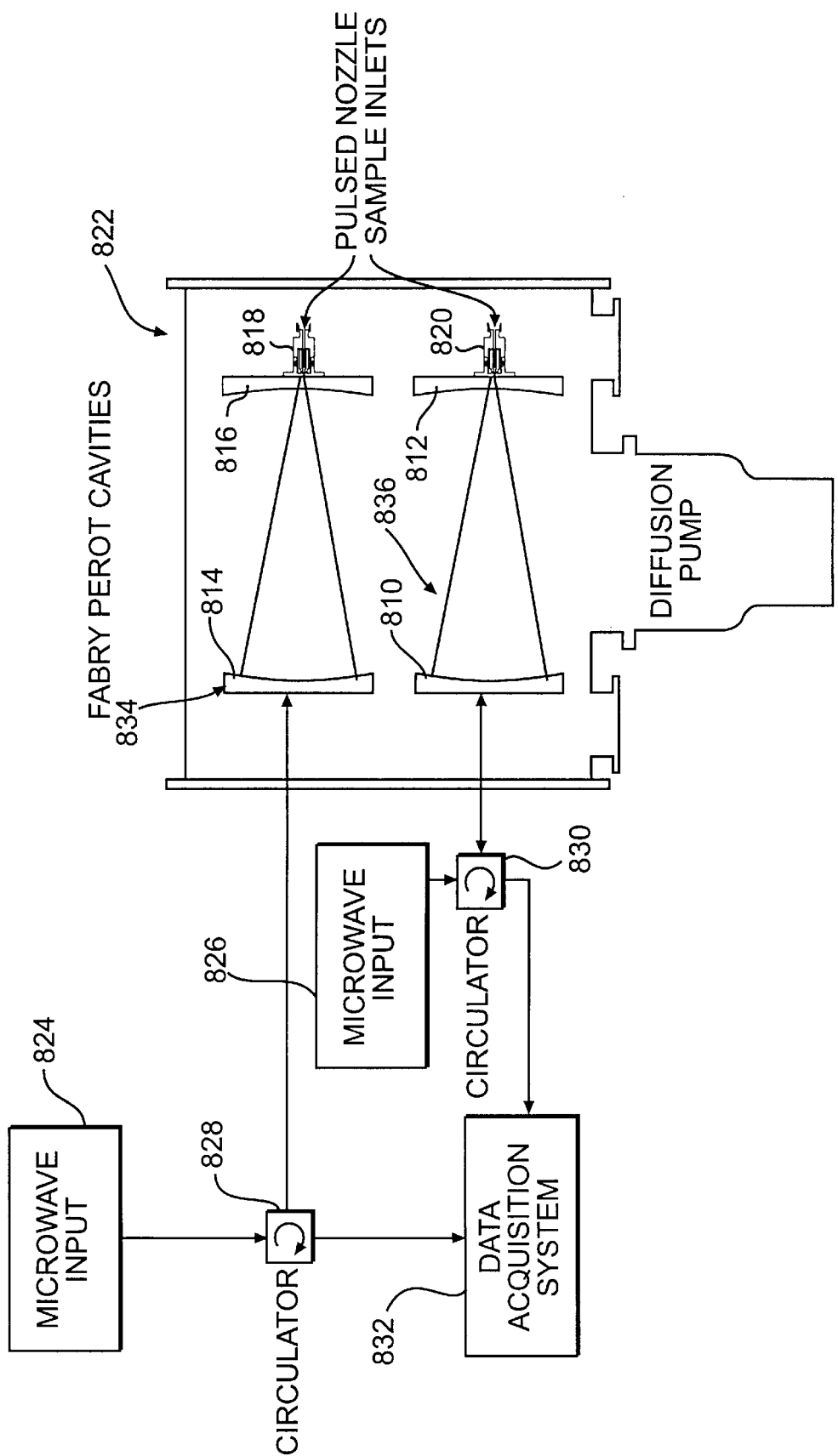
FIG. 8 shows an embodiment of the present invention having two fixed-tuned Fabry-Perot cavities in a single vacuum chamber.

FIG. 8 shows an embodiment of the present invention having two fixed-tuned Fabry-Perot cavities in a single vacuum chamber. Microwave input 824 and circulator 828 direct irradiating microwaves into chamber 822 and cavity 834 through mirror 814 while the gas input nozzle 818 is located at mirror 816. Microwave input 826 and circulator 830 direct irradiating microwaves into chamber 822 and cavity 836 through mirror 810 while the gas input nozzle 820 is located at mirror 812. The data acquisition system 832 is attached to circulators 828 and 830 to monitor and detect the chambered gases and microwaves.

The software system of the present invention has been developed for a 486 personal computer which allows instrument control via a standard mouse using point-and-click techniques. The software employs a Graphical User Interface and is very user-friendly.

OPERATION

Referring again to FIG. 2, the instrument operates by first pulsing a gas sample into Fabry-Perot microwave cavity 215 with pulsed valve 218, then "polarizing" the molecules in the gas sample with a microwave pulse from a broad-banded, (2–26.5 GHz) single-pole double-throw microwave switch 222. Switch 222 feeds a broadbanded, single-sideband modulator 230 which increases the microwave frequency entering the cavity by 30 MHz. The RF switch 224 is pulsed in synchronization with switch 222 to achieve an on/off ratio of 100 dB. This assures that no microwave leakage from the modulator 230 into cavity 215 is present when microwave switch 226 is opened to begin the detection sequence. Switches 222, 224 and 226 also eliminate the use of microwave circulators and isolators which many previous instruments employed. In addition, they allow the instrument to operate over four microwave bands (4–8 GHz, 8–12.4 GHz, 12.4–18.6 GHz, and 18.6–26.5 GHz) without switching microwave hardware components.

Once the microwave cavity is properly tuned to a microwave frequency which corresponds to a rotational transition frequency of a chemical species in the molecular beam, the Fourier components of the microwave pulse pump the rotational transition. Following the microwave pulse the molecular emission signal emanating from the cavity is first amplified with a broad-banded, low-noise microwave amplifier 220 (35 dB gain) which can optionally be cryogenically cooled to further improve the signal-to-noise ratio of the instrument. The amplified signal is then fed into a broad-banded, image-rejection microwave mixer 228 where it is heterodyned with the original output of the microwave synthesizer 232. This image-rejection mixer 228 effectively eliminates noise originating in the opposite sideband thus increasing the signal-to-noise of the instrument by a factor of two. This mixer produces a 30 MHz IF frequency which is further amplified (40 dB) and filtered with a narrow-band 30 MHz filter 234 (1.8 MHz passband). This signal is then digitized in the time domain at 8 MHz (from generator 238) using a 20 MHz digitizer 236. The entire sequence can be run at 10 Hz so averaging is easily done by adding the individual digitized samples.

Microwave synthesizer 232 provides a 10 MHz reference 242, which is fed to pulse controller 240 and to 3× multiplier 244 which then provides a 30 MHz signal to switch 224.

The software package which is used to automate the instrument operates in a Windows-type environment using a graphical user interface (GUI). All components of the instrument are automatically controlled from the computer keyboard and a standard computer mouse. The instrument operates using a standard 80486 processor based personal computer. The software permits automatic tuning of the microwave cavity simply by typing in the desired microwave frequency. The instrument is capable of unattended automated frequency searches. Other options permit automated searches and detection for pre-selected chemical compounds in an unknown sample. Concentration variations as a function of time can also be followed automatically when monitoring a chemical process stream.

This instrument can be used for trace-gas analysis in a variety of analytical chemistry areas, providing real-time detection limits for trace-gas species in the parts-per-billion range.

What is claimed is:

1. A Fabry-Perot cavity Fourier transform microwave spectrometer comprising:

a vacuum chamber;

a first pair of mirrors positioned within said vacuum chamber, forming a Fabry-Perot cavity, each mirror of said first pair of mirrors having a surface with a surface finish of less than or equal to 0.25 microns rms.

2. A microwave spectrometer as in claim 1, wherein said surface of each mirror of said first pair of mirrors is coated with nickel.

3. A microwave spectrometer as in claim 2, wherein said surface of each mirror of said first pair of mirrors is further coated with either gold or silver.

4. A microwave spectrometer as in claim 1, wherein each mirror of said first pair of mirrors has an overall sphericity across its surface of less than or equal to 4 microns rms.

5. A microwave spectrometer as in claim 1, wherein one mirror of said first pair of mirrors forms one end of said vacuum chamber.

6. A microwave spectrometer as in claim 5, further comprising a receiving antenna located in said one mirror of said first pair of mirrors and a microwave amplifier directly connected to said receiving antenna.

7. A microwave spectrometer as in claim 6, wherein a microwave molecular beam is pulsed coaxially into said Fabry-Perot cavity through a pin hole in said one mirror of said first pair of mirrors.

8. A microwave spectrometer as in claim 1, wherein said first pair of mirrors forms a first Fabry-Perot cavity, said microwave spectrometer further comprising a second pair of mirrors positioned within said vacuum chamber, forming a second Fabry-Perot cavity.

9. A microwave spectrometer as in claim 8, wherein said first Fabry-Perot cavity is pre-set to propagate a first fixed microwave frequency and said second Fabry-Perot cavity is pre-set to propagate a second fixed microwave frequency.

10. A microwave spectrometer as in claim 9, wherein a microwave molecular beam is pulsed coaxially into each of said first and second Fabry-Perot cavities through a pin hole in one mirror of the pair of mirrors which forms each cavity.

* * * * *